(12) United States Patent
Sakamoto (10) Patent No.: US 6,471,641 B2
(45) Date of Patent: Oct. 29, 2002

(54) JOINT CONSTRUCTION FOR CONNECTING AN ANGLE SECTION TO A FLEXIBLE BODY SECTION OF ENDOSCOPIC INSERTION INSTRUMENT

(75) Inventor: Kazuhiro Sakamoto, Omiya (JP)

(73) Assignee: Fuji Photo Optical Co., Ltd., Omiya (JP)

( * ) Notice: Subject to any disclaimer, the term of this patent is extended or adjusted under 35 U.S.C. 154(b) by 27 days.

(21) Appl. No.: 09/813,804

(22) Filed: Mar. 22, 2001

(65) Prior Publication Data

US 2002/0026095 A1 Feb. 28, 2002

(30) Foreign Application Priority Data

Mar. 23, 2000 (JP) ........................................ 2000-081513

(51) Int. Cl.[7] .................................................. A61B 1/00
(52) U.S. Cl. ........................ 600/142; 600/139; 600/141
(58) Field of Search ................................. 600/139, 140, 600/141, 142, 146, 149; 604/95.04

(56) References Cited

U.S. PATENT DOCUMENTS

| 4,726,355 | A | * | 2/1988 | Okada | 138/120 |
| 4,807,598 | A | * | 2/1989 | Hasegawa | 600/140 |
| 5,411,020 | A | * | 5/1995 | Ito | 229/87.05 |
| 5,531,664 | A | * | 7/1996 | Adachi et al. | 600/149 |
| 5,591,120 | A | * | 1/1997 | Machida et al. | 138/120 |
| 5,976,074 | A | * | 11/1999 | Moriyama | 600/139 |
| 6,203,494 | B1 | * | 3/2001 | Moriyama | 600/144 |

FOREIGN PATENT DOCUMENTS

| JP | 362208020 A | * | 9/1987 |
| JP | 405038325 A | * | 2/1993 |
| JP | 411225948 A | * | 8/1999 |
| JP | 411235305 A | * | 8/1999 |

* cited by examiner

Primary Examiner—Linda C. M. Dvorak
Assistant Examiner—Kenneth G Schopfer
(74) Attorney, Agent, or Firm—Oblon, Spivak, McClelland, Maier & Neustadt, P.C.

(57) ABSTRACT

In joining an angle section with an elongated flexible body of an endoscopic insertion instrument, a connector ring on the side of the angle section and a connector ring on the side of the flexible body are connected by fitting engagement, one connector ring on the outer side of the other connector ring. A number of inwardly projecting ridges are provided on the inner periphery of the inner connector ring, and screw holes are bored radially through the inwardly projecting ridges. On the other hand, a number of perforations are provided in the outer connector ring at positions corresponding to the screw holes in the inner connector ring. Screw members are threaded into the respective screw holes of the inner connector ring through the perforations in the outer connector ring. Further, a screw anchor ring is slidably fitted on the outer connector ring. The screw anchor ring can be shifted to and from a covering position to close on head portions of the screw members and an uncovering position to uncover and expose head portions of the screw members.

9 Claims, 7 Drawing Sheets

JOINT CONSTRUCTION FOR CONNECTING AN ANGLE SECTION TO A FLEXIBLE BODY SECTION OF ENDOSCOPIC INSERTION INSTRUMENT

BACKGROUND OF THE INVENTION

1. Field of the Art

This invention relates to an insertion instrument of an endoscope for medical use, and more particularly to a joint construction for connecting an angle section to a flexible body section of an endoscopic insertion instrument.

2. Prior Art

Figure 8:
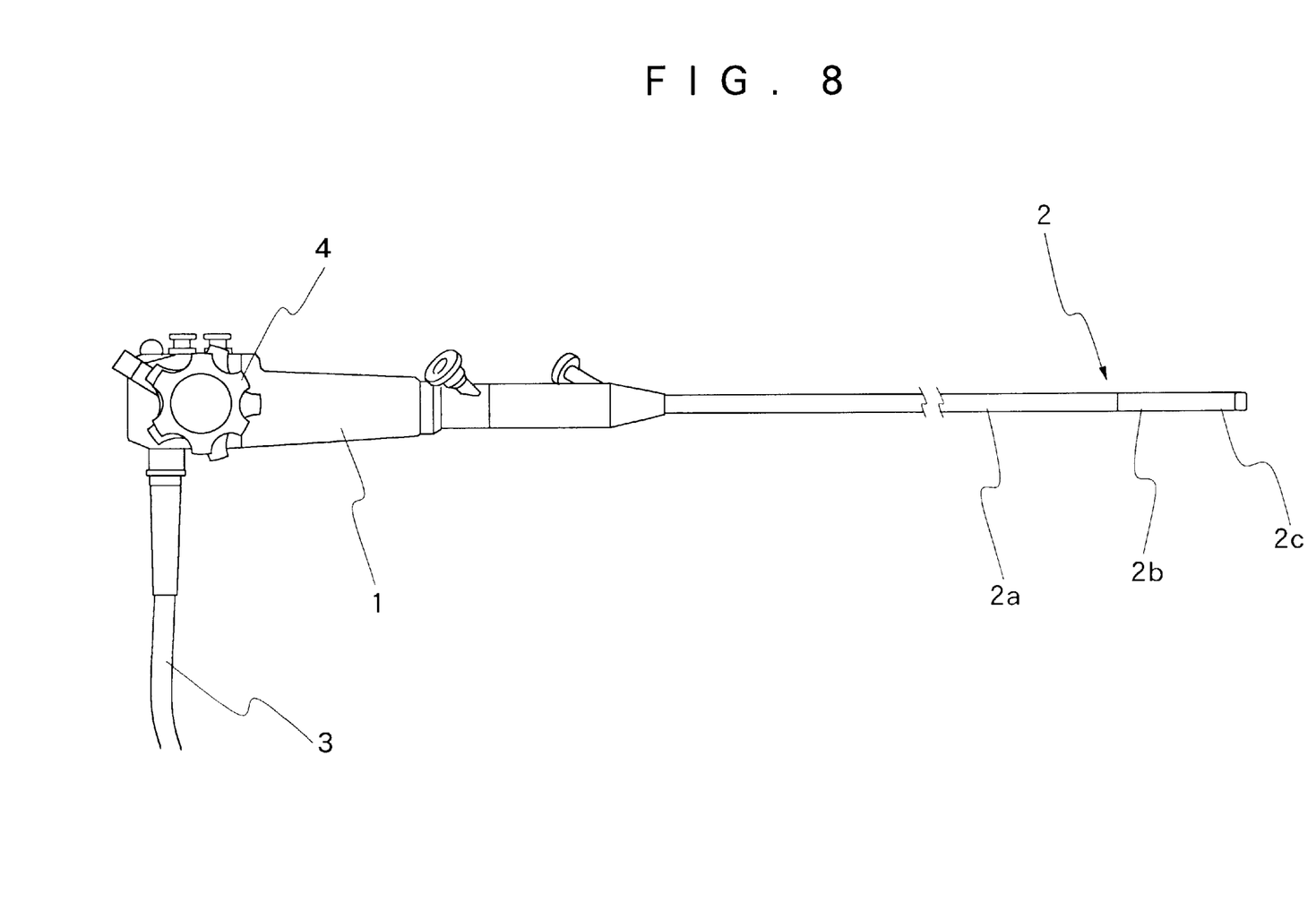
FIG. 8 is an outer view of an endoscope in general use.

Generally, endoscopes which are in use in medical fields have a construction as shown in FIG. 8. In that figure, indicated at 1 is a manipulating head assembly, at 2 an insertion instrument and at 3 a universal cable of an endoscope. A major part of the insertion instrument 2 consists of an elongated flexible body 2a which is extended out from the manipulating head assembly 1. Connected successively to the fore end of the flexible body 2a are an angle section 2b and a rigid tip end section 2c which is provided with an observation window in its housing along with illumination windows. The angle section 2b is interposed for the purpose of turning the rigid tip end section 2c into aimed directions. The elongated flexible body 2a is arranged to have a flexible structure which is bendable in arbitrary directions along a path of insertion.

Figure 9:
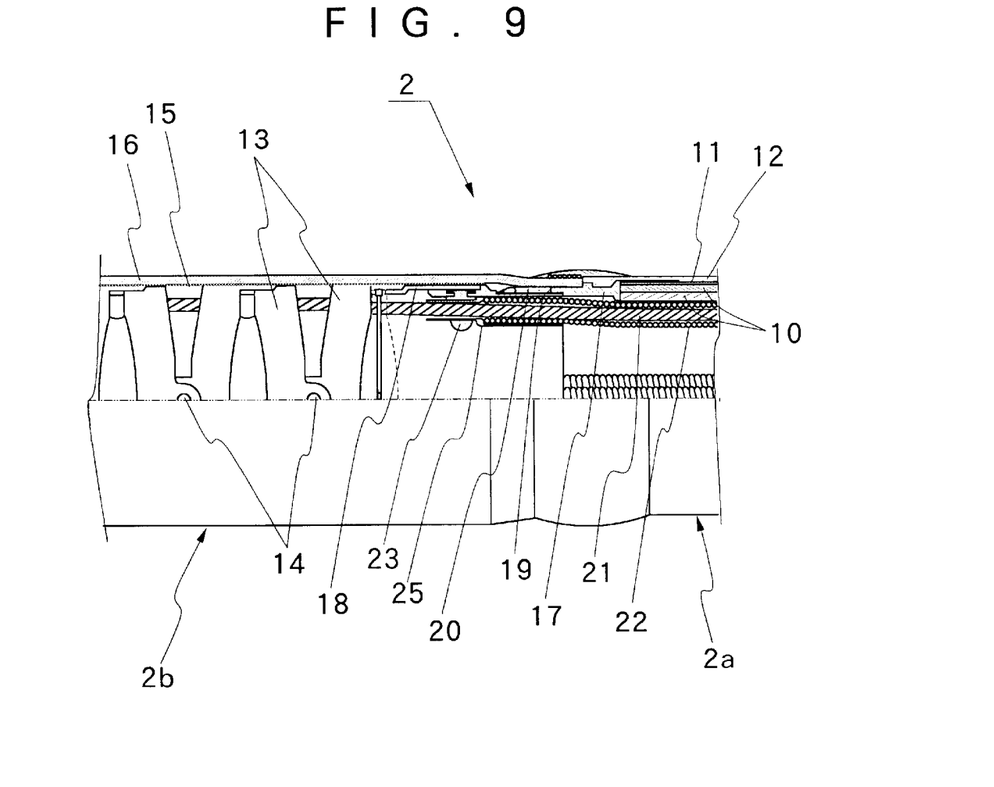
FIG. 9 is a sectional view of a prior art joint construction for connecting an angle section to an elongated flexible body of endoscopic insertion instrument.

Illustrated in FIG. 9 is a joint portion through which the angle section 2b is connected to the flexible elongated body 2a of the insertion instrument 2. Generally, the flexible body 2a, which is required to have flexibility in bending directions, is internally provided with a coil tube as a flexible spinal structure, which is formed by helically winding metal strips of a predetermined width. The coil tube 10 is normally in the form of a double coil tube consisting of two metal coils which are wound in different directions and overlapped one on the other. A mesh layer 11 and an outer skin layer 12 are successively wrapped on and around the coil tube 10 of the flexible body 2a.

The angle section 2b is arranged to be bent into an angular direction by remote control from an angle knob 4 which is provided on the manipulating head assembly 1. The angle section 2b has a flexible structure which is constituted by a series of flexibly connected angle rings 13. Adjacent angle rings 13 are pivotally connected with each other by a pair of pivoting pins 14 which are located at 180 degrees positions relative to each other. Therefore, the angle rings 13 can be turned about the pivoting pins 14 in a direction perpendicular to the axes of the pivoting pins 14. The angle rings 13 are successively connected by the paired pivoting pins 14 the positions of which are shifted alternately by 90 degrees, so that the angle section 2b can be turned vertically in upward and downward directions and at the same time laterally in rightward and leftward directions. Similarly to the flexible body portion 2a, a mesh layer 15 and an outer skin layer 16 are successively wrapped on the pivotally connected angle rings 13.

The flexible body 2a and the angle section 2b of the insertion instrument are different from each other in construction, so that it is the usual practice to fabricate these parts separately and join them together in a later stage. For the purpose of joining the flexible body 2a and the angle section 2b together, connector rings 17 and 18 are attached to the fore end of the flexible body 2a and the proximal end of the angle section 2b, respectively. After being fitted one on the other, the connector rings 17 and 18 are securely fixed with each other. Indicated at 17 is the connector ring on the side of the flexible body 2a. This connector ring 17 is securely fixed to a fore end of the coil tube 10 of the flexible body 2a by spot welding or by other fixation means. On the other hand, indicated at 18 is the connector ring on the side of the angle section 2b. This connector ring 18 is inserted into a rearmost angle ring 13 and likewise securely fixed to the latter by spot welding or by other suitable fixation means. Part of the connector ring 18 on the side of the angle section 2b is fitted into the connector ring 17 on the side of the flexible body 2a. The connector ring 17 which is fitted on the outer periphery of the connector ring 18 is provided with a plural number of perforations 19. Solder is poured into these perforations 19 to fix the outer connector ring 17 to the inner connector ring 18. The outer skin layers 12 and 16 of the flexible body 2a and the angle section 2b are extended to meet on the outer connector ring, and their meeting ends are fixed in position by line wrapping or by the use of an adhesive.

Fitted in or threaded through the endoscopic insertion instrument 2 are various component parts, including a light guide consisting of a bundle of fiber optics for transmission of illumination light, a signal cable in the case of an electronic endoscope (or an image guide consisting of a bundle of fiber optics in the case of an optical endoscope), a biopsy channel for insertion of a biopsy or surgical instrument or the like, and an air/water feed channel. Further, operating wires 21 are threaded internally of the insertion instrument 2 for angularly bending the angle section 2b by remote control. The operating wires 21 include a pair of operating wires which are so arranged and connected as to turn the angle section 2b angularly in upward and downward directions, and another pair of operating wires which are so arranged and connected as to turn the angle section 2b angularly in lateral direction, that is to say, in rightward and leftward directions. The fore ends of these operating wires 21 are securely fixed either to a foremost angle ring of the angle section 2b or to the rigid tip end section 2c. Within the angle section 2b, the operating wires 21 are threaded through the pivoting pins 14 of the angle rings 13 (or through lancing arches which are provided on the angle rings 13). Further a flexible guide tube in the form of a tightly closed coil tube 22 is fitted in the elongated flexible body 2a, and the above-mentioned operating wires 21 are passed through this tightly closed coil 22. The fore end of the tightly closed coil 22 is fixed to a joint portion of the flexible body 2a with the angle section 2b.

Figure 10:
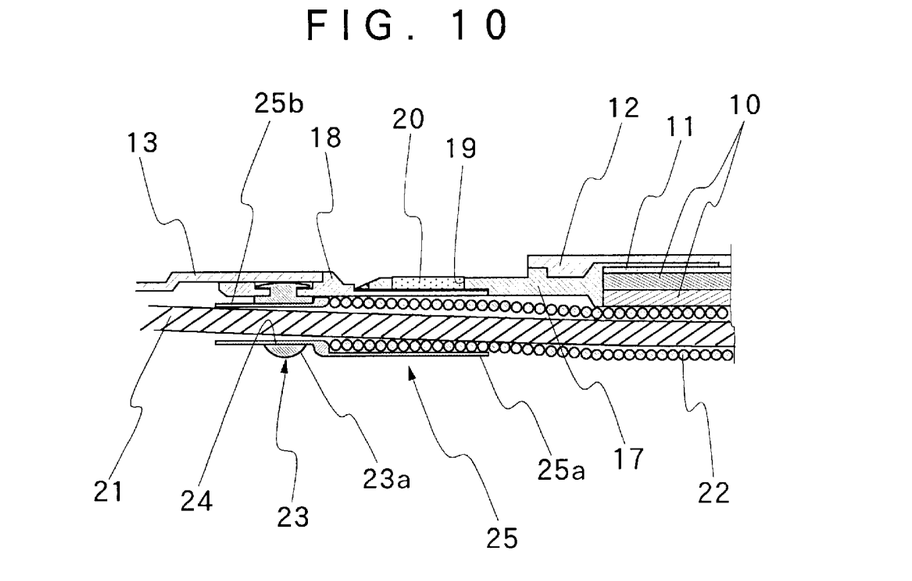
FIG. 10 is an enlarged schematic view of the joint construction shown in FIG. 9.

Illustrated in FIG. 10 is the construction of a fore end portion of the flexible body 2a where the fore end portion of the tightly closed coil 22 is fixed in position. As clear therefrom, by caulking, anchor pins 23 are planted as anchor members in the connector ring 18 on the side of the angle section 2b. A wire passage hole 24 is formed in a head portion 23a of each anchor pin 23, which is located on the inner side of the connector ring 18. Fixedly fitted in the wire passage hole 24 is a pipe member 25 to which the fore end of the tightly closed coil 22 is securely fixed. The fixed pipe member 25 is of a stepped shape having a large diameter portion 25a and a small diameter portion 25b. The fore end of the tightly closed coil 22 is inserted into and securely fixed by soldering to the large diameter portion 25a of the fixed pipe member 25, which is located on the side of the flexible body 2a. The small diameter portion 25b is fitted in the wire passage hole 24, and one operating wire 21 alone is passed through the small diameter portion 25b.

As described above, various component parts are fitted in or threaded internally of the endoscopic insertion instrument 2. Nevertheless, in the event of a trouble with one of the fitted or threaded component parts, namely, in case any one of the fitted component parts is damaged or deformed, it becomes necessary to inspect the interior parts of the insertion instrument and to replace a damaged or deformed part if any. Besides, it may also become necessary to separate the angle section from the flexible body at the time of inspection or troubleshooting. On such an occasion, it has been the usual practice to remove the solder which fixes the connector rings 17 and 18 together. However, the removal of the solder requires not only a special tool but also meticulous skills. In addition, the removal of the solder could result in deformation of or damage to the fixed pipe member 25.

In joining the connector rings 17 and 18 fixedly to each other, the use of solder itself involves a problem that the joint strength varies from one insertion instrument to another. In addition, in order to distribute solder in the gap space between the two connector rings 17 and 18, it is the usual practice to fill a flux into the perforations 19 beforehand. The applied flux, however, may intrude into interior portions of the insertion instrument and contribute to corrosion of the operating wires 21 of the angle section 2b.

In order to avoid the above problems or difficulties, it has also been known in the art to fixedly join the angle section and the flexible body of the insertion instrument by means of screw threads. However, since the angle section 2b is turned and twisted during angling operations, various forces are repeatedly exerted on the joint portion between the angle section and the flexible body of the insertion instrument from different directions, resulting in loosening of the screw threads which join together the angle section and the flexible body.

SUMMARY OF THE INVENTION

In view of the foregoing situations, it is an object of the present invention to provide a joint construction for connecting an angle section to an elongated flexible body of an endoscopic insertion instrument, which can fix the angle section and flexible body firmly with each other in a stable state, while permitting to separate the angle section from the flexible body easily whenever necessary for inspection or for troubleshooting of an internally fitted component part of the insertion instrument.

It is another object of the present invention to provide a joint construction of the sort as mentioned above, which can join an angle section firmly to the elongated flexible body of the insertion instrument without using solder or similar means.

It is still another object of the present invention to provide a joint construction of the sort as mentioned above, which can join the angle section securely with the flexible body of the insertion instrument by the use of screw threads and in such a manner as to prevent loosening of the screw threads.

In accordance with the present invention, for achieving the above-stated objective, there is provided a joint construction for joining an angle section to an elongated flexible body of an endoscopic insertion instrument, which comprises: a connector ring provided at a proximal end of the angle section; a connector ring provided at a fore end of the flexible body and adapted to be connected with the connector ring on the side of the angle section by fitting engagement, with one connector ring on the outer side of the other connector ring; a number of radially inwardly projecting ridge portions provided at angular intervals on an inner periphery of an inner one of the connector rings; screw holes bored in the inner connector ring radially through the inwardly projecting ridge portions; perforations bored in an outer one of the connector rings in radially aligned positions with respect to the screw holes in the inner connector ring; screw members threaded into the screw holes in the inner connector ring through the perforations in the outer connector ring, each one of the screw members having a head portion of a diameter substantially same as that of the perforations; and a screw anchor ring slidably fitted on the outer connector ring for displacement between a covering position to close in at least part of the head portions of the screw members and an uncovering position to totally expose the head portions of the screw members.

Preferably, the inwardly projecting ridge portions are formed in a convex shape in section. The inwardly projecting ridge portions are also adapted to function as guide ways for operating wires which are threaded through the insertion instrument for angularly bending the angle section. For this purpose, wire passage holes are bored axially through the inwardly projecting ridge portions and in such positions as to evade the screw holes, the wire passage holes being in a stepped shape having a large diameter portion on the side of the flexible body and a small diameter portion on the side of the angle section. The operating wires are threaded through the wire passage holes and connected to the angle section, and flexible coils which sheath the operating wires in the flexible body of the insertion instrument have the respective fore ends thereof securely fixed in the large diameter portions of the wire passage holes.

Further, preferably the inwardly projecting ridge portion is provided in four positions approximately at angular intervals of 90 degrees around the inner periphery of the inner connector ring, and the screw holes are formed at least in two of the inwardly projecting ridges to ensure sufficient joint strength between the angle section and the flexible body. In a case where the connector ring on the side of the angle section is fitted on the inner side of the connector ring on the side of the flexible body, a rearmost one of angle rings of the angle section can be used as the connector ring.

In a preferred form of the invention, the screw anchor ring is axially movable on and along the outer connector ring between a covering position to close on the head portions of the screw members and an uncovering position to totally expose the head portions of the screw members. In another preferred form of the invention, the screw anchor ring is provided with openings larger in diameter than the head portions of the screw members, and adapted to be movable in circumferential direction around outer periphery of the outer connector ring to and from a covering position to close on the head portions of the screw members and an uncovering position to expose the head portions of the screw members through the openings.

The above and other objects, features and advantages of the present invention will become apparent from the following particular description of preferred embodiments, taken in conjunction with the accompanying drawings which show by way of example some preferred embodiments of the invention. Needless to say, the present invention should not be construed as being limited to the particular forms shown in the drawings.

DESCRIPTION OF PREFERRED EMBODIMENTS

Figure 1:
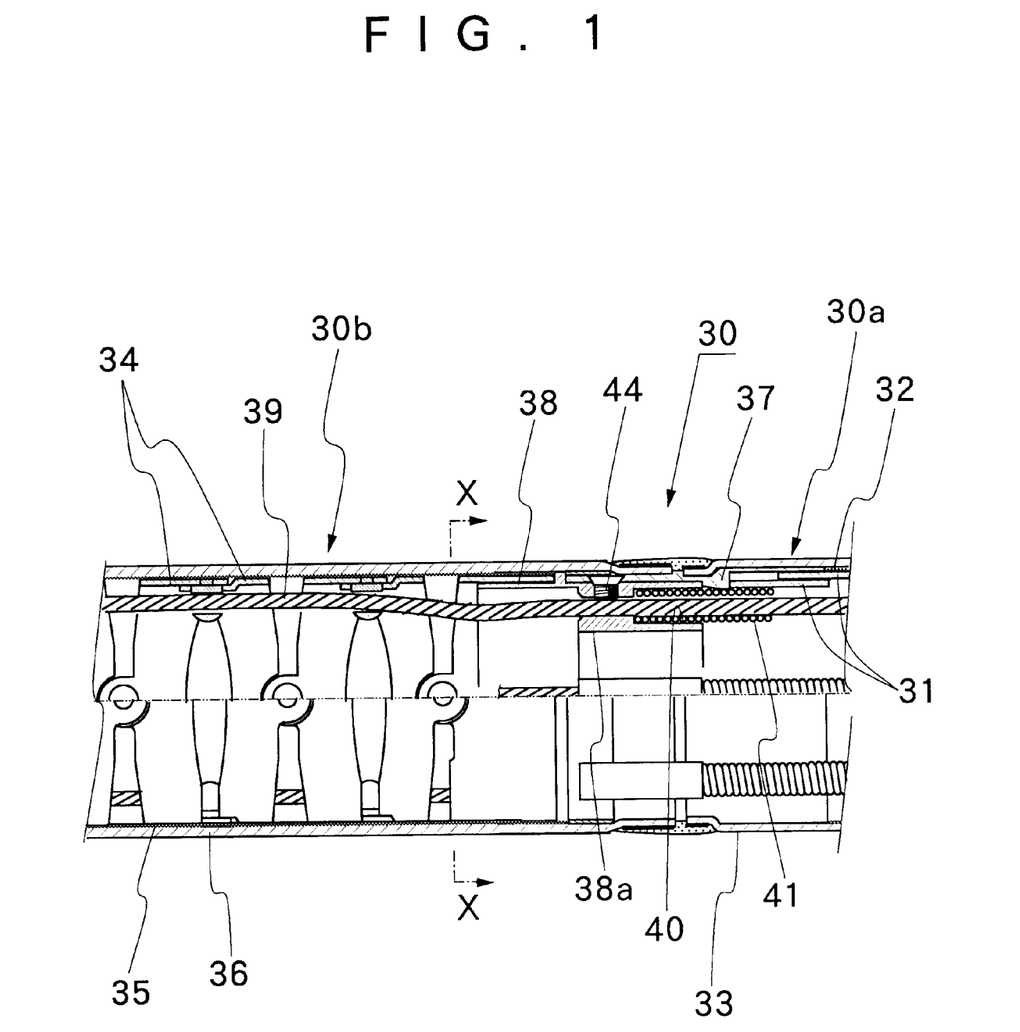
FIG. 1 is a schematic sectional view of a joint portion between an angle section and an elongated flexible body of an endoscopic insertion instrument, embodying the present invention.
Figure 2:
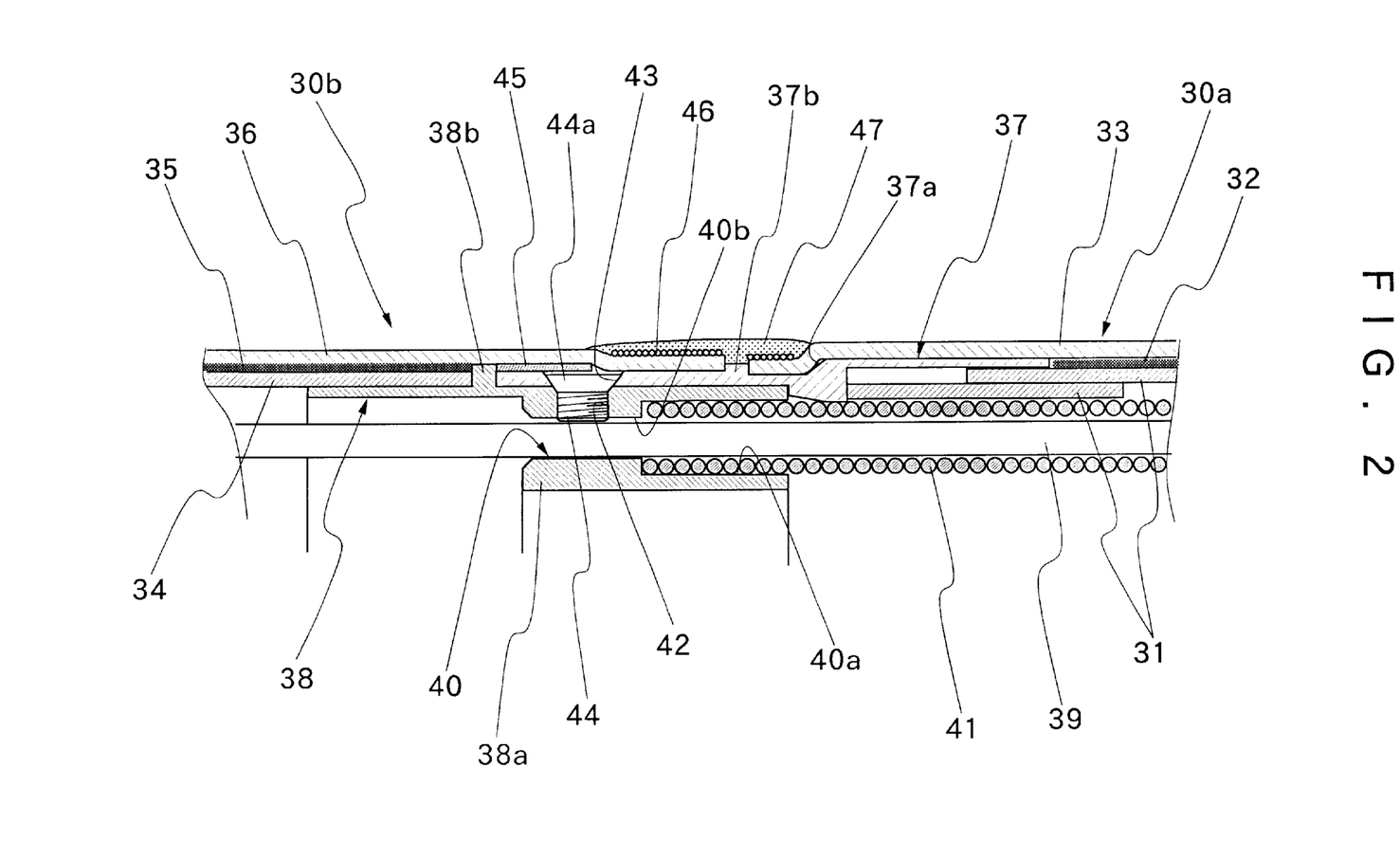
FIG. 2 is an enlarged sectional view of the joint portion shown in FIG. 1.
Figure 3:
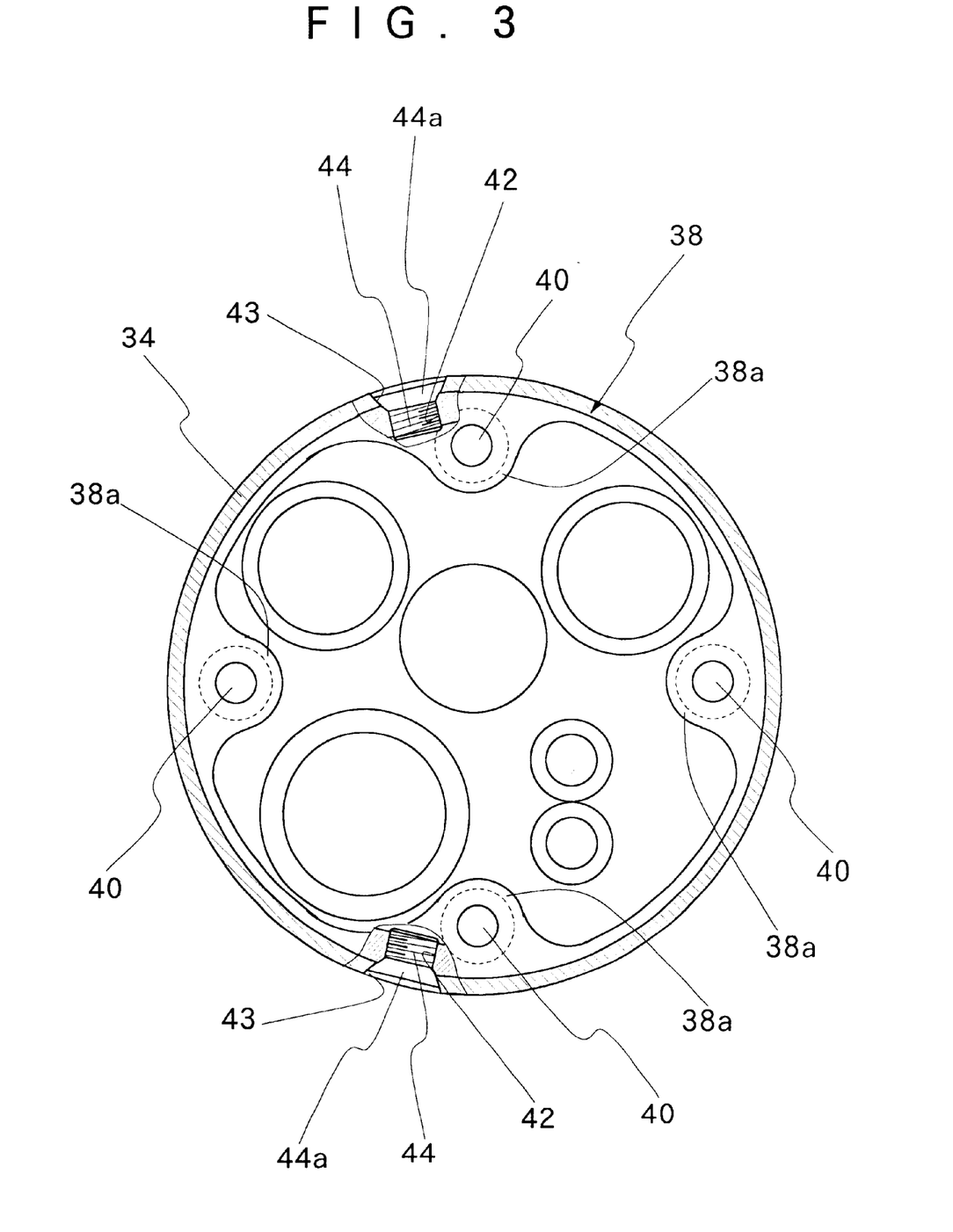
FIG. 3 is a transverse sectional view taken in the direction of arrows X—X in FIG. 1, showing internally fitted component parts of the insertion instrument, and having angle rings, a mesh layer and an outer skin layer of the insertion instrument omitted for the sake of convenience of illustration.

Hereafter, the present invention is described more particularly by way of its preferred embodiments shown in the drawings. FIG. 1 shows in longitudinal section a joint portion which connects an angle section 20b to an elongated flexible body 30a of an endoscopic insertion instrument 30, and FIG. 2 shows the joint portion on an enlarged sectional view taken in the direction of arrows X—X in FIG. 1.

As clear from FIG. 1, the elongated flexible body 30a of the insertion instrument 30 is provided with a double-coil tube 31 as a flexible backbone structure, which is successively wrapped in a mesh layer 32 and an outer skin layer 33. On the other hand, the angle section 30b is provided with a series of pivotally connected angle rings 34 as a flexible backbone structure, which are similarly wrapped in a mesh layer 35 and an outer skin layer 36. A connector ring 37 is securely fixed to a fore end of the coil shaft 31 by soldering or other suitable fixation means. An angle ring 34, which is located in a rearmost position or at a proximal end of the angle section 30b, is adapted to serve as a connector ring 38 on the side of the angle section 30b. These connector rings 37 and 38 are held in fitting engagement with each other over a predetermined axial length.

The connector ring 38 is fitted within the connector ring 37 on the side of the flexible body 30a. The connector ring 38 play the role of connecting the angle section 30b to the flexible body 30a, but it also functions as a position guide for four operating wires 39 which are threaded longitudinally through the insertion instrument 30 at intervals of 90 degrees in the circumferential direction. For this purpose, the connector ring 38 is formed with four inwardly projecting ridges 38a on its inner periphery approximately at intervals of 90 degrees in the circumferential direction. The inwardly projections ridges 38a are in a convexly curved shape in section. If desired, the inwardly projecting ridges 38a may be formed along the entire length of the connector ring 38. However, in the particular embodiment shown, the inwardly projecting ridges 38a are formed to a halfway point of the connector ring 38 from an end on the side of the flexible body 30a.

The operating wires 39 are threaded through passage holes 40 which are bored axially through the inwardly projecting ridge 38 on the inner periphery of the connector ring 38. The passage holes 40 are each in a stepped shape having a large diameter portion 40a on the side of the flexible body 30a and a small diameter portion 40b at the opposite end. On the side of the flexible body 30a of the insertion instrument 30, the operating wires 39 are passed through and sheathed in the tightly closed coils 41, and a fore end portion of each tightly closed coil 41 is fitted and securely fixed in the large diameter portion 40a of the passage hole 40 by spot welding, brazing or other suitable means.

The inwardly projecting ridges 38a in upper and lower position on the inner periphery of the connector ring 38 are each tapped with a radial screw hole 42 in a thickest portion, evading the axial passage hole 40. The connector ring 37 which is fitted around the outer periphery of the connector ring 38 is provided with perforations 43 in positions which correspond to the screw holes 42 in the inwardly projecting ridges 38a on the side of the connector ring 38. A screw 44 with a head portion 44a, which substantially corresponds to the aperture 43 in diameter, is threaded into the screw hole 42 through the perforation 43 in the connector ring 37. Consequently, the connector ring 38 is fixed to the connector ring 37, immovably relative to each other in axial and rotational directions.

The outer periphery of the connector ring 37 is bulged out one the side of its proximal end portion behind a stepped wall portion 37a. Namely, the connector ring 37 is formed in a smaller diameter on the side of its fore end. The fore end of the coil tube 31 is fitted in the large-diameter portion of the connector ring 37 and fixed therein by welding or other suitable fixation means. An annular rib 37b is provided around the outer periphery of the connector ring 37 at an axially intermediate point of the small diameter portion. On the other hand, an annular rib 38b is provided around its outer periphery at a position forward of the inwardly projecting ridges 38a. The annular rib 38b functions as an abutting stopper for the fore end of the other connector ring 37, and is projected slightly radially outward of the outer periphery of the connector ring 37. Fitted on the connector ring 37 is a screw anchor ring 45 which is constituted by a thin metal ring. The screw anchor ring 45 is axially slidable along the connector rings 37 and 38 which are held in fitting engagement with each other. The annular rib 38b on the connector ring 38 and the annular rib 37b on the connector ring 37 functions as stopper members which delimit the axial displacement range of the screw anchor ring 45.

Figure 4:
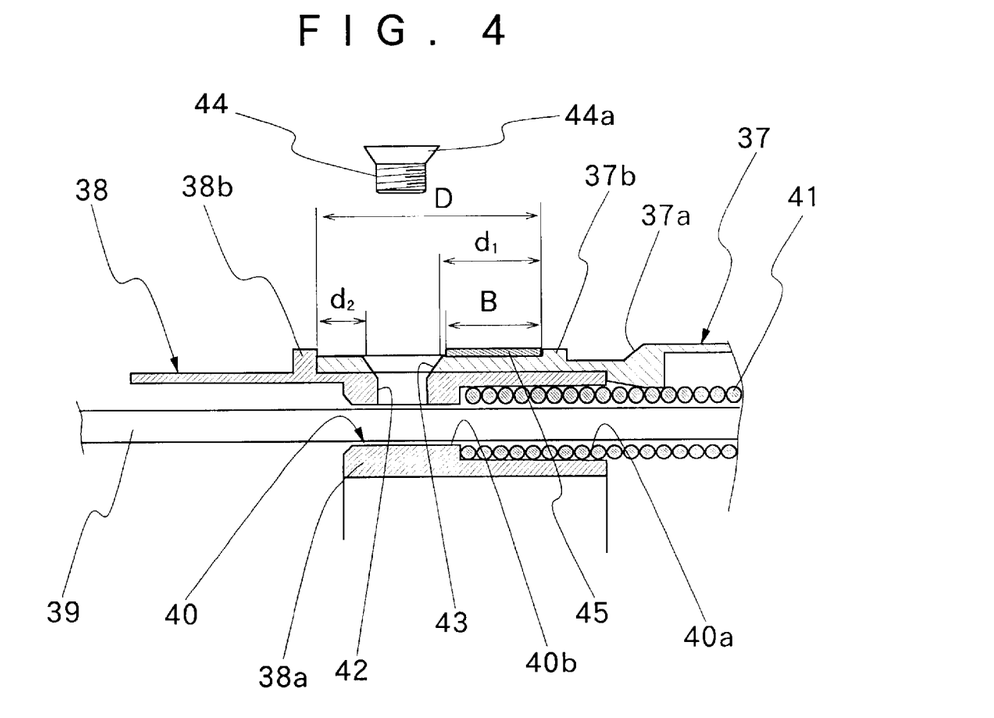
FIG. 4 is a schematic sectional view explanatory of functions of an anchor ring, showing the anchor ring in a position uncovering a head portion of a screw.
Figure 5:
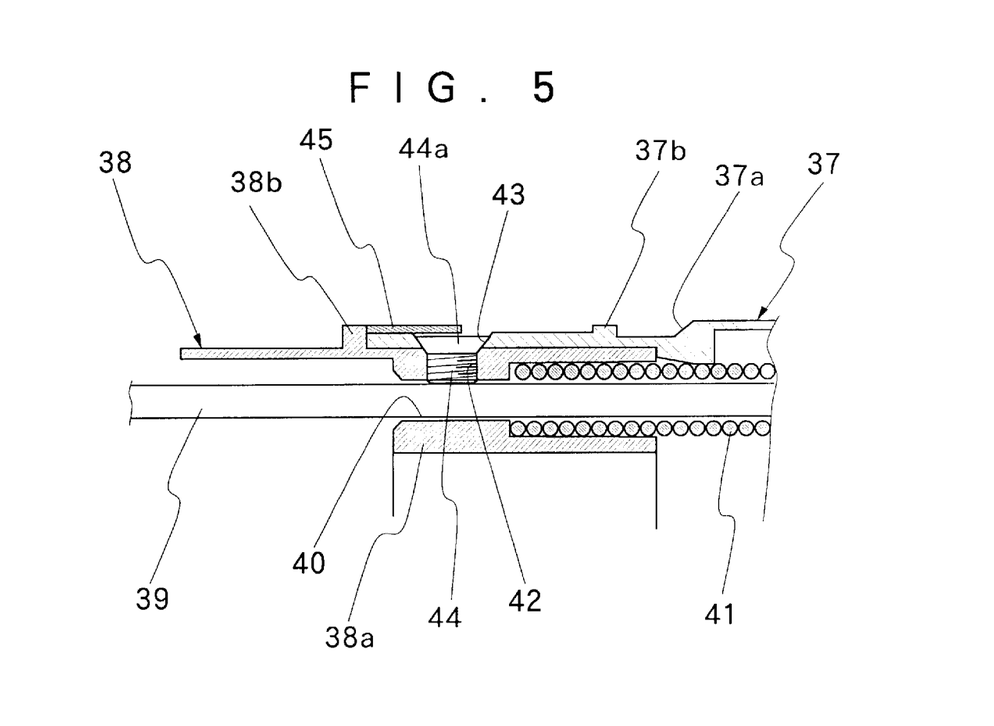
FIG. 5 is a view similar to FIG. 4, showing the anchor ring in a position covering a head portion of a screw.

As shown in FIGS. 4 and 5, the screw anchor ring 45 can be moved axially over a predetermined axial displacement range D between the annular ribs 38b and 37b of the two connector rings 38 and 37. Within the axial displacement range D, the annular rib 37b of the connector ring 37 is located at a distance $d_1$ from a near end of the perforation 43 while the annular rib 38b of the connector ring 38 is located at a distance $d_2$ from the other end of the perforation 43. On the other hand, the screw anchor ring 45 is formed to have a width B, which is in the relationship of $d_1 > B > d_2$. Accordingly, when the screw anchor ring 45 is abutted against the annular rib 37b of the connector ring 37 as shown in FIG. 4, the perforation 43 is exposed in an completely uncovered state. On the other hand, when the screw anchor ring 45 is abutted against the annular rib 38b of the connector ring 38 as shown in FIG. 5, the perforation 43 is at least partially covered under the screw anchor ring 45. In this position, it is preferred that approximately half of the perforation 43 is covered under the screw anchor ring 45. Further, the thickness of the screw anchor ring 45 should preferably be equal with or slightly smaller than the radial projection height of the annular rib 37b.

By the use of the joint construction as described above, the angle section 30b can be firmly and stably connected to the flexible body 30a of the insertion instrument, and at the same time can be easily separated from the flexible body 30a whenever necessary for inspection or troubleshooting of internally fitted component parts of the insertion instrument.

The flexible body 30a and the angle section 30b are connected with each other in the manner as follows. In the first place, while holding the proximal end of the outer skin layer 36 on the side of the angle section 30b in a free state, the screw anchor ring 45 is fitted onto the connector ring 37 on the side of the flexible body 30a. In the next place, the other end of the screw anchor ring 45 is fitted onto the connector ring 38 on the side of the angle section 30b, bringing an end face of the connector ring 37 into abutting engagement with the annular rib 38b of the connector ring 38. In this state, the screw anchor ring 45 is pushed back until it is abutted against the annular rib 37b to uncover the perforation s 43 in the connector ring 37. Thereafter, the connector rings 37 and 38 are turned relative to each other to bring the perforations 43 into alignment with the respective screw holes 42 in radial directions. Then, the screws 44 are threaded into the screw holes 42 through the perforations 43 and tightened to a suitable degree. By so doing, the connector rings 37 and 38 are fixedly connected to each other. Namely, the connector rings 37 and 38 are firmly fixed to each other, without deviations in the axial direction and without relative rotational movements.

After tightening the screws 44, the screw anchor ring 45 is pushed until it is abutted against the annular rib 38b of the connector ring 38. In this position, at least part of the head portion 44a of each screw 44 is covered under the screw anchor ring 45, so that there is no possibility of the screws 44 being unscrewed or loosened, not to mention dislodgement from the respective screw holes. In the next place, the outer skin layer 36 on the side of the angle section 30b is pulled to a position adjoining one side of the annular rib 37b of the connector ring 37. Similarly, the fore end of the outer skin layer 33 on the side of the flexible body 30a is pulled to a position adjoining the other side of the annular rib 37b. Consequently, the outer skin layers 33 and 36 are pulled toward each other and in such a way as to pinch the annular rib 37 between the respective meeting ends. In this regard, depending upon the radial height of the annular rib 37b, the meeting ends of the outer skin layers 33 and 36 may be joined on the annular rib 37 if possible. However, it is not desirable to join the meeting ends of the outer skin layers 33 and 36 in an overlapped state. With the outer skin layers in a joined state, a line wrapping 46 is formed across and around the meeting ends of the outer skin layers 33 and 36, then an adhesive 47 is applied on the line wrapping 46. Thus, the flexible body 30a and the angle section 30b of the insertion instrument are completely joined with each other.

When the flexible body 30a and the angle section 30b are in the joined state as described above, the screw anchor ring 45 is fixedly pressed against the annular rib 38b by the outer skin layer 36 which is fixed in position in a compressed state by the line wrapping 46 and the adhesive 47, covering the head portions 44a of the screws 44. Therefore, by the action of the screw anchor ring 45 which presses the screws 44 inward, there is no possibility of the screws 44 getting loose or being dislodged from the respective positions even if the joint portion is subjected to forces which tend to loosen the screws 44 while the angle section 30b is flexibly turned into various angular positions. Further, at and in a gap space of D–B which exists between an end of the screw anchor ring 45 and the annular rib 37b of the connector ring 37, the outer skin layer 36 is pressed against the connector ring 37 by the line wrapping 46. Therefore, the inside of the insertion instrument 30 is maintained in a hermetically sealed state. Especially high hermetical tightness can be maintained by tightly forming the line wrapping 46 around the outer skin layer 36 which is formed of a resilient material such as urethane rubber, EPDM or the like.

On the other hand, the angle section 30b can be separated from the flexible body 30a by reversing the above-described procedures. Namely, for this purpose, the line wrapping 46 is removed in the first place. Then, the screw anchor ring 45 is moved away from the perforations 47 to remove the screws 44. Upon removable of the screws 44, the angle section 30b is separated from the flexible body 30a of the insertion instrument 30. This means that maintenance and troubleshooting of internally fitted component parts become extremely easily.

In addition, the above-described joint construction does not require soldering and basically employs a mechanical joint mechanism in joining the flexible body 30a and the angle section 30b together, so that it can preclude irregular variations in joint strength from one insertion instrument to another. Further, the angle section can be joined with the flexible body without the use of a flux which might cause corrosion of the operating wires.

Figure 6:
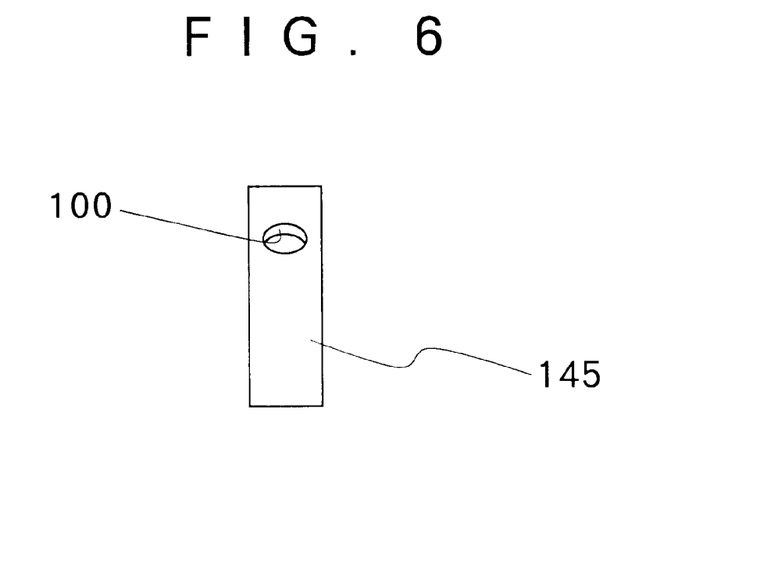
FIG. 6 is a schematic front view of a modification of the anchor ring.
Figure 7:
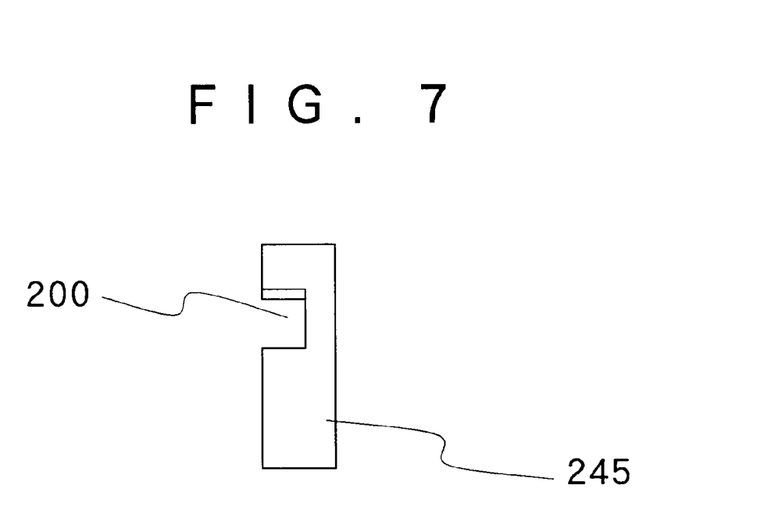
FIG. 7 is a schematic front view of another modification of the anchor ring.

In the above-described embodiment, the screw anchor ring 45 is adapted to be moved axially on and along the outer connector ring 37 to and from a covering position and an uncovering position relative to the perforation 43 which is bored through the connector ring 37. However, in place of the screw anchor ring 45, there may be employed a screw anchor ring 145 with a perforation 100 which is larger than the perforation 43 as shown in FIG. 6, or a screw anchor ring 245 with a notched portion 200 which is wider than the perforation 43 as shown in FIG. 7. In the case of these modifications, the screw anchor ring 145 or 245 is turned through a predetermined angle around the outer connector ring 37 to assume either a covering position where the head of the screw 44 which has been threaded into the connector ring 38 is covered under the screw anchor ring 145 or 245 to prevent loosening, or an uncovering position where the head 44a of the screw 44 is exposed through the perforation 100 or notched portion 200 to permit removal of the screw 44.

What is claimed is:

1. A joint construction for joining an angle section to an elongated flexible body of an endoscopic insertion instrument, comprising:

a connector ring provided at a proximal end of said angle section;

a connector ring provided at a fore end of said flexible body and adapted to be connected with said connector ring on the side of said angle section by fitting engagement, with one connector ring on the outer side of the other connector ring;

a number of radially inwardly projecting ridge portions provided at angular intervals on an inner periphery of an inner one of said connector rings;

screw holes bored in said inner connector ring radially through said inwardly projecting ridge portions;

perforations bored in an outer one of said connector rings in radially aligned positions with respect to said screw holes in said inner connector ring;

screw members threaded into said screw holes in said inner connector ring through said perforations in said outer connector ring, each one of said screw members having a head portion of a diameter substantially same as that of said perforations; and a screw anchor ring slidably fitted on said outer connector ring for displacement between a covering position to close in at least part of said head portions of said screw members and an uncovering position to totally expose said head portions of said screw members.

2. A joint construction for an endoscopic insertion instrument as defined in claim 1, wherein said inwardly projecting ridge portions are formed in a convex shape in section.

3. A joint construction for an endoscopic insertion instrument as defined in claim 1, further comprising wire passage holes bored axially through said inwardly projecting ridge portions and in such positions as to evade said screw holes, said wire passage holes being in a stepped shape having a large diameter portion on the side of said flexible body and a small diameter portion on the side of said angle section, operating wires threaded through said wire passage holes and connected to said angle section for turning same into angularly bent positions, flexible coils sheathing said operating wires in said flexible body of said insertion instrument and having fore ends thereof securely fixed in said large diameter portions of said wire passage holes.

4. A joint construction for an endoscopic insertion instrument as defined in claim 3, wherein said inwardly projecting ridge portions are provided at four positions approximately at angular intervals of 90 degrees around the inner periphery of said inner connector ring, and said screw holes are formed at least in two of said inwardly projecting ridges.

5. A joint construction for an endoscopic insertion instrument as defined in claim 1, wherein said inner connector ring is constituted by a rearmost one of angle rings in said angle section.

6. A joint construction for an endoscopic insertion instrument as defined in claim 1, wherein said screw anchor ring is axially movable on and along said outer connector ring between a covering position to close on said head portions of said screw members and an uncovering position to totally expose said head portions of said screw members.

7. A joint construction for an endoscopic insertion instrument as defined in claim 6, wherein said inner and outer connector rings are each provided with an annular stopper rib around an outer periphery thereof thereby to delimit an axial displacement range of said screw anchor ring.

8. A joint construction for an endoscopic insertion instrument as defined in claim 7, wherein an outer skin layer of said angle section is located between one end of said screw anchor ring and said annular rib after said screw anchor ring is shifted in axial direction into said covering position to close on said head portion of said screw member, and securely fixed in position by line wrapping.

9. A joint construction for an endoscopic insertion instrument as defined in claim 1, wherein said screw anchor ring is provided with openings larger in diameter than said head portions of said screw members, and movable in circumferential direction around outer periphery of said outer connector ring to and from a covering position to close on said head portions of said screw members and an uncovering position to expose said head portions of said screw members through said openings.

* * * * *